United States Patent [19]
Thottathil et al.

[11] Patent Number: 5,274,155
[45] Date of Patent: Dec. 28, 1993

[54] INTRAMOLECULAR ARBUZOV PROCESS FOR THE PREPARATION OF INTERMEDIATES USEFUL IN THE PREPARATION OF PHOSPHORUS CONTAINING HMG-COA REDUCTASE INHIBITORS

[75] Inventors: John K. Thottathil, Robbinsville, N.J.; David Kronenthal, Yardley, Pa.

[73] Assignee: E. R. Squibb & Sons, Inc., Princeton, N.J.

[21] Appl. No.: 986,402

[22] Filed: Dec. 7, 1992

[51] Int. Cl.$^5$ .............................. C07F 7/08; C07F 7/18
[52] U.S. Cl. ..................................... 556/405; 560/56; 560/60; 560/61; 562/466; 562/470; 562/471; 558/179; 558/182; 548/110; 548/119; 548/413; 548/414; 549/4; 549/6; 549/214; 549/218; 549/226
[58] Field of Search ................... 556/405; 560/56, 60, 560/61; 562/466, 470, 471; 558/179, 182; 548/119, 413, 414, 110; 549/6, 4, 218, 214, 222

[56] References Cited
PUBLICATIONS

V. Sawitsch, "Ueber einige vom Aethylen sich ableitende Vervindungen", *Justus Liebig's Annalen der Chemie*, 119, (1861), pp. 182–185.
G. Eglinton et al., "The Coupling of Acetylenic Compounds", *Advan. Org. Chem*, 4, 91963), pp. 225–328.

*Primary Examiner*—Paul F. Shaver
*Attorney, Agent, or Firm*—Ellen K. Park

[57] ABSTRACT

A process for the preparation of compounds of formula

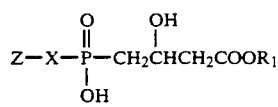

and pharmaceutically acceptable salts thereof; wherein X is —CH$_2$—, —CH$_2$CH$_2$—, —CH$_2$CH$_2$CH$_2$—, —CH=CH—, —C≡C— or —CH$_2$O— (where O is linked to Z); Z is a hydrophobic anchor R$_1$ is hydrogen, alkyl, cycloalkyl or aryl; comprising the steps of:

(A) reacting a compound of formula

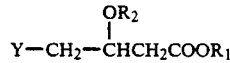

with a compound of formula

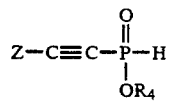

or a compound of formula

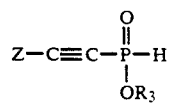

in the presence of an amine base or an alkali metal hydride in an organic solvent to form a compound having the formula

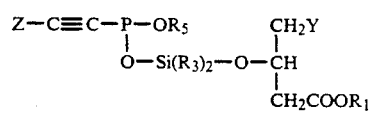

(B) heating the compound of formula IX at a temperature of from about 100° C. to about 200° C., to form a compound of formula

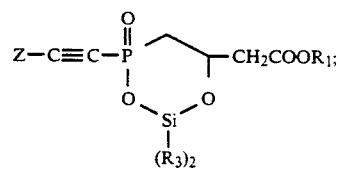

and
(C) quenching the compounds of formula VIII with an acid provides the compounds of formula I.

10 Claims, No Drawings

INTRAMOLECULAR ARBUZOV PROCESS FOR THE PREPARATION OF INTERMEDIATES USEFUL IN THE PREPARATION OF PHOSPHORUS CONTAINING HMG-COA REDUCTASE INHIBITORS

FIELD OF THE INVENTION

This invention relates to a process for the preparation of intermediates useful in the preparation of compounds which inhibit the activity of 3-hydroxy-3-methylglutaryl coenzyme A (HMG-CoA) reductase. The instant invention also relates to the novel intermediates produced.

BACKGROUND OF THE INVENTION

U.S. Pat. No. 5,091,378 discloses HMG-CoA reductase inhibitors which have the formula:

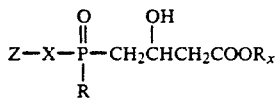

wherein R is hydroxy or lower alkoxy; $R_x$ is hydrogen or lower alkyl; X is —CH$_2$—, —CH$_2$CH$_2$—, —CH$_2$CH$_2$CH$_2$—, —CH=CH—, —C≡C—, or —CH$_2$O—, (where O is linked to Z); and Z is a hydrophobic anchor. The disclosure of U.S. Pat. No. 5,091,378 is incorporated by reference herein.

Examples of such compounds having the above formula include (S)-4-[[[1-(4-fluorophenyl)-3-(1-methylethyl)-1H-indol-2-yl]ethynyl]hydroxyphosphinyl]-3-hydroxybutanoic acid, or its sodium salt (SQ 33,600) (preferred) or its dilithium salt;

(S)-4-[[(E)-2-[4'-fluoro-3,3',5-trimethyl[1,1'-biphenyl]-2-yl]ethenyl]hydroxyphosphinyl]-3-hydroxybutanoic acid or its dilithium salt;

(S)-4-[[2-[4'-fluoro-3,3',5-trimethyl[1,1'-biphenyl]-2-yl]ethyl]hydroxyphosphinyl]-3-hydroxybutanoic acid, methyl ester or mono- or di-alkali metal salts thereof;

(S)-4-[[[4'-fluoro-3,3',5-trimethyl[1,1'-biphenyl]-2-yl]ethynyl]methoxyphosphinyl]-3-hydroxybutanoic acid or the methyl ester thereof;

(5Z)-4-[[2-[4'-fluoro-3,3',5-trimethyl[1,1'-biphenyl]-2-yl]ethenyl]hydroxyphosphinyl]-3-hydroxybutanoic acid, methyl ester thereof;

(S)-4-[[2-[3-(4-fluorophenyl)-1-(1-methylethyl)-1H-indol-2-yl]ethyl]methoxyphosphinyl]-3-hydroxybutanoic acid, methyl ester;

(S)-4-[[2-[[1,1'-biphenyl]-2-yl]ethyl]methoxyphosphinyl-3-hydroxybutanoic acid, methyl ester;

(S)-4-[[2-[4 '-fluoro-3,3',5-trimethyl[1,1'-biphenyl]-2-yl]ethyl]hydroxyphosphinyl]-3-hydroxybutanoic acid, dilithium salt;

(S)-4-[[2-[4'-fluoro-3,3',5-trimethyl[1,1'-biphenyl]-2-yl]ethynyl]hydroyphosphinyl]-3-hydroxybutanoic acid, dilithium salt;

(SZ)-4-[[2-[4'-fluoro-3,3',5-trimethyl[1,1'-biphenyl]-2-yl]ethenyl]hydroxyphosphinyl]-3-hydroxybutanoic acid, dilithium salt;

(S)-4-[[2-[3-(4-fluorophenyl)-1-(1-methylethyl)-1H-indol-2-yl]ethyl]hydroxyphosphinyl]-3-hydroxybutanoic acid, dilithium salt;

(S)-4-[[2-[(1,1'-biphenyl]-2-yl]ethyl]hydroxyphosphinyl]-3-butanoic acid, dilithium salt;

(S)-4-(hydroxymethoxyphosphinyl)-3-[[(1,1-dimethylethyl)diphenylsilyl]oxy]butanoic acid, methyl ester, or its dicyclohexylamine (1:1) salt;

(E)-4-[[2-[3-(4-fluorophenyl)-1-(1-methylethyl)-1H-indol-2-yl]ethenyl]hydroxyphosphinyl]-3-hydroxybutanoic acid or its dilithium salt or methyl ester thereof;

4-[[2-[4'-fluoro-3,3',5-trimethyl[1,1'-biphenyl]-2-yl]ethyl]hydroxyphosphinyl]-3-hydroxybutanoic acid or its dilithium salt or methyl ester thereof;

(E)-4-[[2-[4'-fluoro-3,3',5-trimethyl[1,1'-biphenyl]-2-yl]ethenyl]hydroxyphosphinyl]-3-hydroxybutanoic acid or its dilithium salt or methyl ester thereof;

(S)-4-[[[2,4-dimethyl-6-[(4-fluorophenyl)methoxy]phenyl]ethyl]hydroxyphosphinyl]-3-hydroxybutanoic acid or its dilithium salt or methyl ester thereof;

(S)-4-[[[2,4-dimethyl-6-[(4-fluorophenyl)methoxy]phenyl]ethynyl]hydroxyphosphinyl]-3-hydroxybutanoic acid or its dilithium salt or methyl ester thereof;

(S)-4-[[2-[3,5-dimethyl[1,1'-biphenyl]2-yl]ethyl)hydroxyphosphinyl]-3-hydroxybutanoic acid or its dilithium salt or methyl ester thereof;

(S)-4-[[2-[4'-fluoro-3,5-dimethyl[1,1'-biphenyl]-2-yl]ethyl]hydroxyphosphinyl]-3-hydroxybutanoic acid or its dilithium salt or methyl ester thereof;

(S)-4-[[2-[[1,1'-biphenyl]-2-yl]ethynyl]hydroxyphosphinyl]-3-hydroxybutanoic acid or its dilithium salt or methyl ester thereof;

(S)-4-[[2-(5-(4-fluorophenyl)-3-(1-methylethyl)-1-phenyl-1H-pyrazol-4-yl]ethynyl]methoxyphosphinyl]-3-hydroxybutanoic acid, methyl ester;

(S)-4-[[2-[1-(4-fluorophenyl)-3-(1-methylethyl)-1-indol-2-yl]ethynyl]hydroxyphosphinyl]-3-hydroxybutanoic acid or its dilithium salt or disodium salt or methyl ester thereof;

(S)-4-[[2-[1-(4-fluorophenyl)-3-(1-methylethyl)-1H-indol-2-yl]ethyl]hydroxyphosphinyl]3-hydroxybutanoic acid or its dilithium salt or methyl ester thereof;

(S)-4-[[2-[5-(4-fluorophenyl)-3-(1-methylethyl)-1-phenyl-1H-pyrazol-4-yl]ethynyl]hydroxyphosphinyl]-3-hydroxybutanoic acid, dilithium salt;

(E)-4-[[2-[5-(4-fluorophenyl)-3-(1-methylethyl)-1-phenyl-1H-pyrazol-4-yl]ethenyl]methoxyphosphinyl]-3-hydroxybutanoic acid, methyl ester;

(E)-4-[[2-[5-(4-fluorophenyl)-3-(1-methylethyl)-1-phenyl-1H-pyrazol-4-yl]ethenyl]hydroxyphosphinyl]-3-hydroxybutanoic acid, dilithium salt;

(S)-4-[[2-[5-(4-fluorophenyl)-3-(1-methylethyl)-1-phenyl-1H-pyrazol-4-yl]ethyl]methoxyphosphinyl]-3-hydroxybutanoic acid, methyl ester;

(S)-4-[[2-[5-(4-fluorophenyl)-3-(1-methylethyl)-1-phenyl-1H-pyrazol-4-yl]ethyl]hydroxyphosphinyl]-3-hydroxybutanoic acid, dilithium salt;

(S)-4-[[2-[3-(4-fluorophenyl)-5-(1-methylethyl)-1-phenyl-1H-pyrazol-4-yl]ethyl]methoxyphosphinyl]-3-hydroxybutanoic acid, methyl ester;

(S)-4-[[2-[3-(4-fluorophenyl)-5-(1-methylethyl)-1-phenyl-1H-pyrazol-4-yl]ethyl]hydroxyphosphinyl]-3-hydroxybutanoic acid, dilithium salt;

(S)-4-[[2-[3-(4-fluorophenyl)-5-(1-methylethyl)-1-phenyl-1H-pyrazol-4-yl]ethynyl]methoxyphosphinyl]-3-hydroxybutanoic acid, methyl ester;

(S)-4-[[2-[3-(4-fluorophenyl)-5-(1-methylethyl)-1-phenyl-1H-pyrazol-4-yl]ethynyl]hydroxyphosphinyl]-3-hydroxybutanoic acid, dilithium salt;

(S)-4-[[[4-(4-fluorophenyl)-1-(1-methylethyl)-3-phenyl-1H-pyrazol-5-yl]ethynyl]methoxyphosphinyl]-3-hydroxybutanoic acid, methyl ester;

(S)-4-[[[4-(4-fluorophenyl)-1-(1-methylethyl)-3-phenyl-1H-pyrazol-5-yl]ethynyl]hydroxyphosphinyl]-3-hydroxybutanoic acid, dilithium salt;

(S)-4-[[2-[4-(4-fluorophenyl)-1-(1-methylethyl)-3-phenyl-1H-pyrazol-5-yl]ethyl]methoxyphosphinyl]-3-hydroxybutanoic acid, methyl ester;

(S)-4-[[2-[4-(4-fluorophenyl)-1-(1-methylethyl)-3-phenyl-1H-pyrazol-5-yl]ethyl]hydroxyphosphinyl]-3-hydroxybutanoic acid, dilithium salt;

(S)-4-[[[1-(4-fluorophenyl)-4-(1-methylethyl)-2-phenyl-1H-imidazole-5-yl]ethynyl]methoxyphosphinyl]-3-hydroxybutanoic acid, methyl ester;

(S)-4-[[[1-(4-fluorophenyl)-4-(1-methylethyl)-2-phenyl-1H-imidazol-5-yl]ethynyl]methoxyphosphinyl]-3-hydroxybutanoic acid, methyl ester;

(S)-4-[[2-[1-(4-fluorophenyl)-4-(1-methylethyl)-2-phenyl-1H-imidazol-5-yl]ethyl]methoxyphosphinyl]-3-hydroxybutanoic acid, methyl ester;

(S)-4-[[2-[1-(4-fluorophenyl)-4-(1-methylethyl)-2-phenyl-1H-imidazol-5-yl]ethyl]hydroxyphosphinyl]-3-hydroxybutanoic acid, dilithium salt;

(S)-4-[[[2-(cyclohexylmethyl)-4,6-dimethylphenyl]ethynyl]hydroxyphosphinyl]-3-hydroxybutanoic acid or its dilithium salt or methyl ester thereof;

4-[[2-[2-(cyclohexylmethyl)-4,6-dimethylphenyl]ethenyl]hydroxyphosphinyl]-3-hydroxybutanoic acid or its dilithium salt or methyl ester thereof;

(S)-4-[[2-[2-(cyclohexylmethyl)-4,6-dimethylphenyl]ethyl]hydroxyphosphinyl]-3-hydroxybutanoic acid or its dilithium salt or methyl ester thereof;

4-[[[[4'-fluoro-3,3',5-trimethyl[1,1'-biphenyl]-2-yl]oxy]methyl]hydroxyphosphinyl]-3-hydroxybutanoic acid or its dilithium salt or methyl ester thereof;

4-[[[4'-fluoro-3,3',5-trimethyl[1,1'-biphenyl]-2-yl]methyl]hydroxyphosphinyl]-3-hydroxybutanoic acid or its dilithium salt or methyl ester thereof;

(S)-4-[[[1-(4-fluorophenyl)-3-methyl-2-naphthalenyl]ethynyl]hydroxyphosphinyl]-3-hydroxybutanoic acid or its dilithium salt or methyl ester thereof;

(E)-4-[[2-[1-(4-fluorophenyl)-3-methyl-2-naphthalenyl]ethenyl]hydroxyphosphinyl]-3-hydroxybutanoic acid or its dilithium salt or methyl ester thereof;

(S)-4-[[2-[1-(4-fluorophenyl)-3-methyl-2-naphthalenyl]ethyl]hydroxyphosphinyl]-3-hydroxybutanoic acid or its dilithium salt or methyl ester thereof;

4-[[3-[4'-fluoro-3,3',5-trimethyl[1,1'-biphenyl]-2-yl]propyl]methoxyphosphinyl]-3-hydroxybutanoic acid, methyl ester;

4-[[3-[4'-fluoro-3,3',5-trimethyl[1,1'-biphenyl]-2-yl]propyl]hydroxyphosphinyl]-3-hydroxybutanoic acid, dilithium salt;

[1S-[1α(R*),2α,4aβ,8β,8aα]]-4-[[2-[8-(2,2-dimethyl-1-oxobutoxy)decahydro-2-methyl-1-naphthalenyl]ethyl]methoxyphosphinyl]-3-hydroxybutanoic acid, methyl ester;

[1S-[1α(R*),2α,4aβ,8β,8aβ]]-4-[[2-[8-(2,2-dimethyl-1-oxobutoxy)decahydro-2-methyl-1-naphthalenyl]ethyl]hydroxyphosphinyl]-3-hydroxybutanoic acid, dilithium salt;

(S)-4-[[[3'-(4-fluorophenyl)spiro]cyclopentane-1,1'-[1H]indene]-2-yl]ethynyl]methoxyphosphinyl]-3-hydroxybutanoic acid, methyl ester; and (S)-4-[[[3'-(4-fluorophenyl)spiro]cyclopentane-1,1'-[1H]indene]-2-yl]ethynyl]hydroxyphosphinyl]-3-hydroxybutanoic acid, dilithium salt.

BRIEF DESCRIPTION OF THE INVENTION

The instant invention provides a process for preparation of compounds of formula

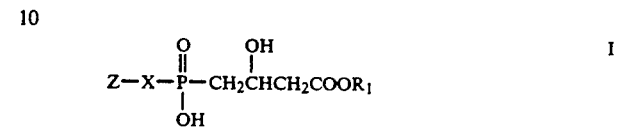

where X and Z are as defined previously with respect to U.S. Pat. No. 5,091,378; and $R_1$ is hydrogen, alkyl, cycloalkyl or aryl.

The process for the preparation of compounds of formula I comprises the steps of:

(A) preparing a compound of formula

where Y a halogen, preferably iodine; and $R_2$ is a radical of formula $-SiW(R_3)_2$, where W is chlorine, bromine, alkoxy or dialkylamine and $R_3$ is alkyl or cycloalkyl;

(B) reacting a compound of formula II with a compound of formula

where $R_4$ is trialkylsilyl or triarylsilyl; or a compound of formula

in the presence of an amine base or an alkali metal hydride in an organic solvent to form a compound having the formula

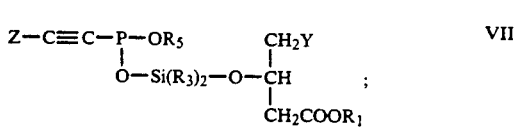

where $R_5$ is $R_3$ when compounds of formula II are reacted with compounds of formula VI or $R_4$ when compounds of formula II are reacted with compounds of formula V;

(C) heating the compound of formula VII at a temperature of from about 100° C. to about 200° C., to form a compound of formula

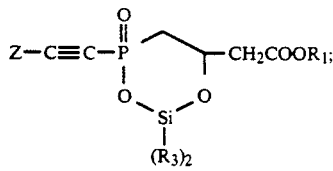

and (D) quenching the compounds of formula VIII with an acid to provide the compounds of formula I.

Compounds of formula I are useful intermediates in the preparation of HMG-CoA reductase inhibitors, which are useful for example, in the treatment of hypercholesterolemia, hyperlipoproteinemia, hyperlipodemia and atherosclerosis. The instant invention provides a convenient process for the preparation of compounds of the formula I in good yields.

DETAILED DESCRIPTION OF THE INVENTION

Listed below are definitions of various terms used to describe this invention. These definitions apply to the terms as they are used throughout the specification (unless they are otherwise limited in specific instances) either individually or as part of a larger group.

The term "alkyl" includes both straight and branched chain hydrocarbons, containing 1 to 12 carbon atoms in the normal chain, preferably 1 to 7 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethyl serityl, nonyl, decyl, undecyl, dodecyl, the various branched chain isomers thereof, and the like as well as substituted groups, including the following substituents: halo, alkoxy, aryl, alkylaryl, haloaryl, cycloalkyl, alkylcycloalkyl, hydroxy, alkylamine, alkanoylamino, nitro, cyano, thiol or alkylthio.

The term "lower alkyl" includes an alkyl group as described above having from 1 to 6, preferably 1 to 4 carbon atoms.

The term "alkenyl" refers to such groups as described above for "alkyl", further containing at least one carbon to carbon double bond. Those groups having 2 to 10 carbon atoms are preferred.

The term "alkynyl" refers to such groups as described above for "alkyl", further containing at least one carbon to carbon triple bond. Those groups having 2 to 10 carbon atoms are preferred.

The term "cycloalkyl" includes saturated cyclic hydrocarbon groups containing 3 to 12 carbons, preferably 3 to 8 carbons, which include cyclopropyl, cyclobutyl, and the like, any of which groups may be substituted with halogens, alkyl, alkoxy, hydroxy and the like.

The term "alkoxy" or "lower alkoxy" includes an alkyl or lower alkyl group, as described above, linked to an oxygen atom.

The term "aryl" refers to phenyl and substituted phenyl. "Substituted phenyl" refers to a phenyl group substituted with 1, 2 or 3 amino, halogen, hydroxyl, trifluoromethyl, alkyl (of 1 to 4 carbon atoms), alkoxy (of 1 to 4 carbon atoms), alkanoyloxy, aminocarbonyl, or carboxy groups. Exemplary substituted phenyl groups are substituted with 1, 2 or 3 amino, alkylamino, dialkylamino, nitro, halogen, hydroxyl, trifluoromethyl, alkyl (of 1 to 4 carbon atoms), alkoxy (of 1 to 4 carbon atoms) alkanoyloxy, carbamoyl or carboxyl groups.

The term "alkanoyl" as used herein refers to alkyls linked to a carbonyl group.

The term "halogen" or "halo" includes fluorine, chlorine, bromine and iodine.

The term "salt(s)" refers to acidic and/or basic salts formed with inorganic and organic acids and bases. Basic salts are preferred. Exemplary basic salts include ammonium salts, alkali metal salts such as lithium, sodium and potassium salts (which are preferred), alkaline earth metal salts such as the calcium and magnesium salts, salts with organic bases, for example, amine salts such as dicyclohexylamine salt, benzathine, N-methyl-D-glucamine, hydrabamine salts, salts with amino acids such as arginine and lysine and equivalent such salts. The nontoxic, pharmaceutically acceptable salts are preferred, although other salts are also useful, for example, in isolation or purification steps which may be employed during preparation.

The instant invention provides a process for preparation of compounds of formula

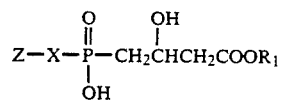

where X and Z are as defined previously with respect to U.S. Pat. No. 5,091,378; and $R_1$ is hydrogen, alkyl, cycloalkyl or aryl.

Compounds of formula I where X is —C≡C— may be prepared by:

(A) preparing a compound of formula

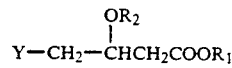

where Y a halogen, preferably iodine; and $R_2$ is a radical of formula —SiW($R_3$)$_2$, where W is chlorine, bromine, alkoxy or dialkylamine and $R_3$ is alkyl or cycloalkyl;

(B) reacting a compound of formula II with a compound of formula

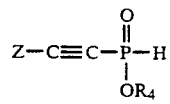

where $R_4$ is trialkylsilyl or triarylsilyl; or a compound of formula

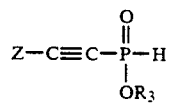

in the presence of an amine base or an alkali metal hydride in an organic solvent to form a compound having the formula

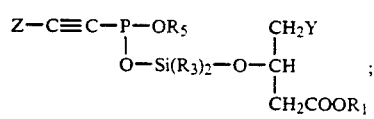

where $R_5$ is $R_3$ when compounds of formula II are reacted with compounds of formula VI or $R_4$ when compounds of formula II are reacted with compounds of formula V;

(C) heating the compound of formula VII at a temperature of from about 100° C. to about 200° C., to form a compound of formula

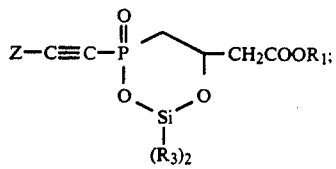

and (D) quenching the compounds of formula VIII with an acid to provide the compounds of formula I.

In step (A) a compound of the formula

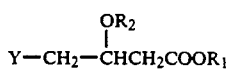

where Y is iodine is prepared by: (1) treating a halohydrin of formula

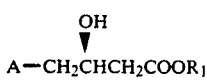

where A is bromine or chlorine, with an iodide ion in an organic solvent to form an iodohydrin of formula

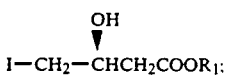

and (2) treating a compound of formula IV with a silane to provide the compounds of formula II where Y is iodine. The iodide ion may be provided by sodium iodide, potassium iodide or tetrabutylammonium iodide. Suitable organic solvents include acetone, methyletheyl ketone, methyl isobutyl ketone or dimethylformamide. The method of step (1) above, is preferably conducted at a temperature of from about 80° C. to about 120° C. The halohydrin of step (1) where A is bromine is commercially available. An exemplary silane is dimethyldichlorosilane, which is also commercially available. Compounds of formula II where Y is bromine or chlorine may be prepared by modifying the methods disclosed above. Compounds of formula II where Y is iodine are preferred.

Compounds of the formula

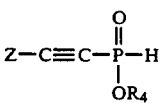

may be prepared by:

(1) phosphorylating a compound of formula

using for example, phosphorus tribromide in an organic solvent such as methylene chloride, 1,2-dichloroethane or carbon tetrachloride and quenching the product with a base such as sodium hydroxide, sodium ethoxide, potassium t-amylate, lithium hydroxide or tetrabutyl ammonium hydroxide, to form the intermediates of formula

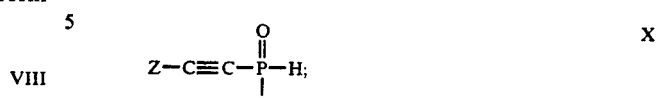

and (2) silylating the compound of formula X with one equivalent of a silylating agent to form the silyl ester of formula V. Exemplary silylating agents include trimethylsilylchloride, N,O-bis-(trimethylsilyl)-acetamide or N,O-bis-(trimethylsilyl)-trifluoroacetamide.

The starting material (compounds of formula IX) for preparing compounds of formula V, may be prepared by methods disclosed in U.S. Pat. No. 5,091,378 cited above. Alternatively, compounds of formula IX may be prepared by: (1) reacting compounds of formula

with an alkylating agent such as carbon tetrachloride or carbon tetrabromide and a reducing agent such as triethylphosphite in an inert organic solvent such as methylene chloride, 1,2-dichloroethane or acetonitrile, at temperatures from about −20° C. to about −40° C. to form a compound of formula

where hal and hal' are the same or different halogen; and (2) reacting the compounds of formula XII with a base such as sodium ethoxide, sodium methoxide, potassium t-butoxide or potassium t-amylate or similar bases in the presence of a reducing agent such as diethylphosphite or dimethylphosphite or similar phosphites to form the compounds of formula IX.

Compounds of formula XI may be prepared by the skilled artisan. For example, the compounds of formula XI may be prepared as disclosed in U.S. Pat. No. 5,091,378 cited above.

Compounds of the formula

may be prepared by: (1) converting a compound of formula

to a phosphonite intermediate by deprotonation with a base such as n-butyllithium, lithium hexamethyl disilazide or lithium diisopropylamide in an organic solvent such as tetrahydrofuran, toluene or heptane; and treating the product with a (R₃)₂halophosphite such as diethylchlorophosphite; (2) quenching with an aqueous solution of an organic or inorganic base such as saturated sodium bicarbonate, triethylamine or potassium bicarbonate; and (3) subjecting the product of step (2) to extractive work-up and controlled hydrolysis in the presence of a catalytic amount of acid such as p-toluenesulfonic acid to produce the compounds of formula VI.

Compounds of formula X may also be prepared by hydrolysis of compounds of formula VI with an aqueous acid or base such as HCl, sodium hydroxide or tosic acid or alternatively by hydrolysis of the phosphonite intermediate formed in step (1) above (for forming compounds of formula VI) with acids such as hydrochloric acid.

In step (B), a compound of the formula

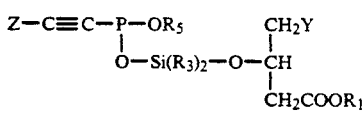   VII where $R_5$ is $R_4$, is prepared by reacting a compound of formula II with a compound of formula V in the presence of an amine base or an alkali metal hydride in an organic solvent.

Alternatively, compounds of formula VII (where $R_5$ is $R_3$) may be prepared by reacting a compound of formula II with a compound of formula VI in the presence of an amine base or an alkali metal hydride in an organic solvent.

Any amine base or alkali metal hydride effecting the reaction of formula II with formula V or formula VI may be employed. Exemplary amine bases are triethylamine or 1,8-diazabicyclo[5.4]undec-7-ene. An exemplary alkali metal hydride is sodium hydride. Suitable organic solvents for step (B) include toluene, xylene, heptane, chloroform, dichloromethane, tetrahydrofuran or dioxane.

The method of step (B) is preferably conducted at a temperature of from about 0° C. to about 40° C.

In step (C), a compound of formula

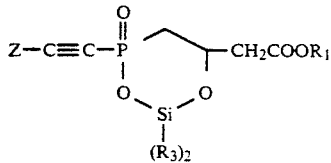   VIII is prepared by heating compounds of formula VII at a temperature of from about 100° C. to about 200° C. The method of step (C) is preferably conducted at a temperature of from about 130° C. to about 150° C. for about 5 to 15 hours.

Finally, quenching the compounds of formula VIII with an acid such as hydrochloric acid provides the compounds of formula I.

All stereoisomers of the compounds of the instant invention are contemplated, either in admixture or in pure or substantially pure form.

Although the procedures above have been described for the preparation of compounds of formula I, where X is —C≡C—, compounds of formula I where X is —CH₂—, —CH₂CH₂—, —CH₂CH₂CH₂—, —CH═CH— or —CH₂O— (where O is linked to Z) may be prepared by modifying the procedures described herein by a skilled artisan.

Preferred compounds of the formula I are those where X is —C≡C—; Z is the hydrophobic anchor:

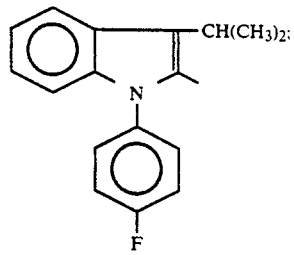

and $R_1$ is hydrogen, alkyl, cycloalkyl or aryl.

The compounds of formula I, prepared as described herein may be employed in the preparation of inhibitors of the enzyme HMG-CoA reductase, such as those of formula A, by methods described in the previously cited U.S. Pat. No. 5,091,378.

An exemplary process for forming compounds of formula A, employing the compounds of formula I includes: (1) converting compounds of formula I to a salt of formula

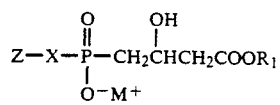   XIII using amine or alkali metal bases such as α-methylbenzylamine, 1-adamantanamine or cinchonidine or by exchange with an alkalai metal carboxylate or sulfonate; (2) saponifying compounds of formula XIII to the diacid of formula

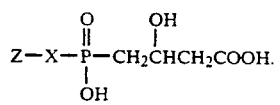   XIV

Compounds of formula XIV may be further titrated with a base such as sodium hydroxide to produce the preferred final product of formula

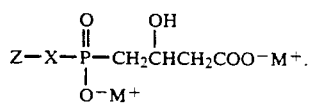   XV

Alternatively, the diacid may be converted to a mono amine salt or mono alkali metal salt (sodium preferred) for the purpose of purification. Further, compounds of formula I may be saponified directly to the diacid of formula XIV optimally using an alkalai metal hydroxide such as sodium hydroxide, potassium hydroxide or lithium hydroxide or a quaternary ammonium hydroxide.

The following examples and preparations describe the manner and process of making and using the invention and are illustrative rather than limiting. It should be understood that there may be other embodiments which fall within the spirit and scope of the invention as defined by the claims appended hereto.

EXAMPLE 1

[[1-(4-Fluorophenyl)-3-(1-methylethyl)-1H-indol-2-yl]ethynyl] phosphinic acid

A. 1-(4-Fluorophenyl)-3-(1-methylethyl)-1H-indole2-carboxyaldehyde

1. 4-Methyl-2-oxopentanoic ethyl ester

4-Methyl-2-oxopentanoic acid, sodium salt (25 g) was dissolved in a minimum amount of water, acidified to pH 1 with concentrated hydrochloric acid and then extracted several times with methylene chloride. The aqueous phase was saturated with sodium chloride and back-extracted (twice) with methylene chloride. The combined organic phases were washed with brine, dried over anhydrous sodium sulfate and evaporated in vacuo to give 17.7 g (82.8% recovery) of the free acid as a viscous oil.

A mixture of the acid (17.7 g, 136 mmol) in dry benzene (200 mL) was treated with 1,8-diazobicyclo[5.4.0]undec-7-ene (20.4 mL, 136.2 mmol, 1 eq) giving an exothermic reaction (heat of crystallization) and a gel-like crystalline salt formed. The mixture was treated with ethyl iodide (10.9 mL, 1 eq) and mechanically stirred under argon for three hours. Precipitated salts were removed by filtration, the filtrate was washed once with a small amount of water (50 mL) and brine, then dried over anhydrous sodium sulfate. Benzene was removed by distillation at atmospheric pressure and the yellow liquid remaining was vacuum distilled to give 6.46 g (35.1%) of the title compound as a clear, pale yellow liquid with boiling point equaling 65°–66° C. (5 mm Hg).

2. 4-Methyl-2-(phenylhydrazono)pentanoic acid, ethyl ester

A solution of the title 1 compound (5 g, 31.6 mmol) in dry methylene chloride (30 mL) was treated with phenylhydrazine (3.3 mL, 33.2 mmol, 1.05 eq) dropwise over five minutes and the yellow mixture stirred under argon at room temperature over 4A sieves for three hours. The mixture was dried over anhydrous sodium sulfate, filtered and evaporated in vacuo to give 8.105 g of an orange oil. The crude oil was purified by flash chromatography on LPS-1 silica gel (30:1) eluting with (97:3) hexane-ethyl acetate. Product fractions were evaporated to give 6.8 g (86%) of pure title compound and 848 mg (10.8%) of the geometrical isomer of the title compound. Total yield=97.5%

3. 3-(1-Methylethyl)-1H-indole-2-carboxylic acid, Ethyl Ester

Gaseous hydrogen chloride was bubbled (gas dispersion tube) into a dry absolute ethanolic (50 mL, over 3A sieves) solution of the title 2 compound (6.8 g, 27.4 mmol) for 30 minutes at room temperature. The exothermic reaction was characterized by color changes from yellow to red to deep green followed by precipitation of white ammonium chloride. The suspension was stirred an additional 20 minutes under Drierite, then dumped into ice cold water (50 mL). Ethanol was removed in vacuo and the residue partitioned between ethyl acetate and water. The aqueous layer was extracted with ethyl acetate (twice), the combined organic phases washed with water and brine, then dried over anhydrous sodium sulfate and evaporated in vacuo to give 4.969 g of a green solid. The crude solid was dissolved in hot hexane, treated with Darco, filtered through packed Celite, concentrated to a 30–50 mL volume and the yellow solution allowed to crystallize. Precipitated crystals were collected by filtration, rinsed with cold hexane and dried to give 4.34 g (68.5%) of pure title compound as white needles with melting point equaling 80° to 81° C. TLC (9:1) hexane-acetone, $R_f$=0.42, UV & PMA. $R_f$ of the title 2 and title 3 compounds were identical but the title 3 compound had a bright purple fluorescence.

4. 1-(4-Fluorophenyl)-3-(1-methylethyl)-1H-indole-2-carboxylic acid, ethyl ester A solution of the title 3 compound (3.937 g, 17 mmol) and 1-bromo-4-fluorobenzene (9.34 mL, 85 mmol, 5 eq) in dry dimethyl formamide (15 mL) was treated with cuprous oxide (245 mg, 1.7 mmol, 0.1 eq) and refluxed under argon for 17 hours. Additional bromide (9.34 mL, 5 eq) and cuprous oxide (245 mg, 0.1 eq) were added, refluxing continued for six hours, more cuprous oxide added (730 mg, 5.1 mmol) and refluxing continued for 60 more hours. Dimethyl formamide and excess bromide were distilled off in vacuo and the orange residual oil taken up in ethyl acetate, filtered through packed Celite, washed with saturated sodium bicarbonate and brine, then dried over anhydrous sodium sulfate and evaporated to give 5.385 g (97.2%) of desired crude title compound as an orange oil.

5. 1-(4-Fluorophenyl)-3(1-methylethyl)-1H-indole-2-methanol

To cold (0° C., ice bath) dry ethyl ether (24 mL) under argon was added solid lithium aluminum hydride (907 mg, 23.9 mmol, 1.5 molar eq) followed by dropwise addition of the title 4 compound (5.185 g, 15.9 mmol) in dry ethyl ether (10 mL) over 10 minutes. The mixture was stirred for 1 hour at 0° C., then quenched at 0° C. by sequential dropwise addition of water (910 μl), 15% sodium hydroxide (910 μl) and water (2.73 mL). The suspension was filtered through anhydrous magnesium sulfate over packed Celite and the filtrate evaporated to a clear, colorless oil. The oil gradually crystallized from hexane to give in 2 crops (3.771 g and 0.333 g) 4.10 g (90.9%) of pure title compound as white, granular crystals with melting point equalling 81° C. to 82° C.

6. 1-(4-Fluorophenyl)-3-(1-methylethyl)-1H-indole-2-carboxaldehyde

A solution of Dess-Martin periodinane (6.46 g, 15.24 mmol) in dry methylene chloride (30 mL) was treated with dry t-butanol (4 Å sieves, 1.44 mL, 15.24 mmole, 1.0 eq) and the mixture stirred under argon for 15 minutes at room temperature. A solution of the title 5 compound; (3.599 g, 12.7 mmol) in dry methylene chloride (13 mL) was added dropwise over 10 minutes and the pale yellow mixture stirred under argon at room temperature for 30 minutes. The reaction mixture was added to a solution of sodium thiosulfate (14.06 g 89 mmole, 7 eq) in freshly prepared 1N sodium bicarbonate (40 mL) and stirred for 10 minutes. The aqueous phase was drawn off, the organic phase washed with 1.0N sodium bicarbonate (twice), water, and brine, then dried over anhydrous sodium sulfate and evaporated in vacuo to give 3.877 g of a yellow oil. The crude oil was purified by flash chromatography on LPS-1 silica gel (40:1) eluting with (40:1) Hexane:ethylene oxide. Product fractions were evaporated to give 3.118 g (87.3%, crude yield) of product plus an impurty (same $R_f$ as product). One recrystallization from hot hexane gave 2.643 g (74%, 76% corrected yield based on recovered alcohol)

of pure title compound as white fluffy needles with melting point equalling 114° to 116° C.

B. 2-(2,2-Dibromoethenyl)-1-(4-fluorophenyl)-3-(1-methylethyl)-1H-indole

To a solution of the title A compound (98.4 g, 0.35 mol) and carbon tetrabromide (243.6 g, 2.1 eq, 0.735 mol) in 750 mL of methylene chloride was added dropwise a solution of triethyl phosphite (1.47 mol, 4.2 eq. 252 mL) in 100 mL of methylene chloride with mechanical stirring over a period of 45 minutes to one hour. During the addition, the internal temperature was maintained between −37° C. to −25° C. After the addition was complete, the reaction temperature was raised to −20° C. over a 30 minute period and then poured into 250 mL of saturated sodium bicarbonate and 100 g of ice. At the 30 minute period, the TLC indicated that the reaction was over. Hexane:ethyl acetate; 96:4; silica gel; PMA, UV and iodine visualization; $R_f$: 0.35 (s.m.); 0.75 (product).

The organic layer was separated and the aqueous layer was extracted with methylene chloride (300 mL×1). The combined organic layer was washed with saturated sodium bicarbonate (200 mL×2), half saturated sodium chloride (200 mL×2; to remove the possible remaining sodium bicarbonate from the organic layer), brine (200 mL×2) and dried over magnesium sulfate. The organic layer was filtered and concentrated on a rotavap. The crude reaction product is a mixture of liquid and solid. The residue thus obtained was dissolved in 180 mL of acetonitrile by heating on a steam bath with occasional shaking. It was left at room temperature for 4 hours and then in a cold room over night. The crystal mass was filtered and washed with cold hexane (100 mL) to give 127 g (80%) of the title compound. This material was recrystallized from hexane (3.5 mL/g) to provide 113 g of the title compound. Melting point: 121° C. to 123.5° C.

C. 2-Ethynyl-1-(4-fluorophenyl)-3-(1-methyethyl)-1H-indole

To a mechanically stirred solution of the title B compound (21 g, 48 mmol) in 144 mL of toluene at 0° C. was added dropwise a toluene solution of potassium tert-amylate (30.1 mL, 1.13 eq, 54.2 mmol) over a period of 20 minutes, maintaining the internal temperature at ∼5° C. After the addition was complete, TLC (silica gel; Toluene: Hexane, 1:9 $R_f$=0.36 for bromoacetylene, 0.3 for the title B compound) showed complete elimination of the title B compound to the bromoacetylene.

Methanol (9.71 mL, 5 eq, 240 mmol) and dimethyl phosphite (5.72 mL, 1.3 eq, 62.4 mmol) were added sequentially to the reaction mixture, which was then cooled to 0° C. The addition of the initial one-tenth amount of methanol and dimethyl phosphite was exothermic and the order of addition was important to prevent the Arbuzov reaction. Methanol was added before the the addition of dimethylphosphite. A toluene solution of potassium tert-amylate (28 mL, 1.05 eq, 50.4 mmol) was added dropwise to the yellow and cloudy solution over a period of 30 minutes while maintaining the internal temperature at ∼5° C. The solution became light yellow and cloudy at the end of the addition. After the addition was complete, the reaction was stirred at ∼5° C. for an additional 20 minutes (TLC: silica gel; Toluene: Hexane, 1:9. $R_f$=0.36 for bromoacetylene, 0.3 for the title B compound). The light yellowish solution was poured into ice-cold saturated ammonium chloride (200 mL). The organic layer was washed with water (100 mL×2), saturated sodium bicarbonate (100 mL×2), half-saturated sodium chloride (100 mL×2), and brine (100 mL×1) and dried over magnesium sulfate.

Following filtration and concentration, hexane (30 mL) was added to the residue to azeotropically remove the trace toluene and the residue became a grey solid. The solid residue was dissolved in 50 mL hexane (∼45° C.). Then it was filtered through a silica gel (8 g) and Celite cake. The height of the silica gel in a 2×1¾ inches filter funnel was 0.4 inches. On top of this silica gel another 0.4 inches Celite was added before filtering the solution. The cake was washed with an additional 45 mL hexane. The total volume of the solution was reduced to two-thirds under reduced pressure and then it was seeded and set aside at room temperature for 1 hour and at 4° C. overnight. The solution was decanted and the crystals were washed with cold hexane (5 mL×2). After drying, 10.5 g of the title compound was obtained as a white solid (80%).

D. [[1-(4-Fluorophenyl)-3-(1-methylethyl)-1H-indol-2-yl]ethynyl] phosohinic acid To a mechanically stirred methylene chloride (35 mL) solution of the title C compound (5.0 g, 18.1 mmol) at ambient temperature under argon was added dropwise a neat portion of phosphorus tribromide (3.8 mL, 39.7 mmol). The resulting amber clear solution was stirred at this temperature overnight. The reaction mixture was poured into a 1N sodium hydroxide solution with ice-cooling. The aqueous solution was acidified to pH 2 with 6N HCl. After stirring for 15 minutes the suspension was filtered and air-dried to give a white solid (1.4 g). The remaining acidified aqueous layer was extracted with ethyl acetate. (100 mL×2). The combined organic layer was washed with half-saturated sodium chloride (100 mL×3), brine (100 mL×1), dried over anhydrous sodium sulfate, filtered, and concentrated on a rotovapor to 50 mL of the total volume. Hexane (65 mL) was added to this solution. The resulting homogeneous solution was heated at room temperature for 45 minutes and then placed in a cold room for 16 hours. The solid was filtered and air-dried to give a fine, white solid (2.4 g). The total amount of title compound obtained was 3.8 g (61% yield from two crops).

EXAMPLE 2

(S)-3-[(Chlorodimethylsilyl)oxy]-4-iodo-butanoic acid, methyl ester

A. (S)-3-Hydroxy-4-iodobutanoic acid, methyl ester

A solution of (S)-4-Bromo-3-hydroxybutanoic acid, methyl ester (14.822 g, 75.2 mmol) in methyl ethyl ketone (255 mL) was treated with anhydrous sodium iodide (56.6 g, 376 mmol). The resulting red mixture was stirred for 23 hours under argon at a bath temperature of 92° C. The solution was allowed to cool to room temperature and the solids were filtered through celite. The receiver flask was switched and the celite bed was washed with ethyl acetate (3×50 mL). The original MEK product-rich filtrate was concentrated to approximately 60 mL. The residue was treated with the ethyl acetate wash from above followed by 250 mL of fresh ethyl acetate. The solution was washed with sodium sulfite solution (2×100 mL), brine (1×75 mL) and dried (sodium sulfate). Filtration followed by concentration in vacuo produced a yellow liquid which was evaporated several times from hexane and dried under high vacuum (5 mm) to 15.48 g (84%).

B. (S)-3-[(Chlorodimethylsilyl)oxy]-4-iodobutanoic acid, methyl ester

A dry, 1-L, 3-necked flask was charged with dichloromethane (450 mL) and cooled to −10° C. under argon. Dimethyldichlorosilane (63 mL) was slowly added followed by triethylamine (16.6 mL, 118 mmol) dropwise. A solution of the title A compound (24 g, 98.36 mmol) in dichloromethane (50 mL) was added dropwise. The mixture was stirred at −10° C. for one hour, and then at room temperature for four hours. Heptane (500 mL) was added to the reaction and the resulting mixture was stirred for 20 minutes and filtered through celite. The filtrate was concentrated in vacuo and re-filtered through celite using heptane to wash the celite. The filtrate was concentrated in vacuo and distilled (88° C., 0.01 mm) to produce 2.99 g (28%) of the title compound.

EXAMPLE 3

(S)-4-[[[1-(4-Fluorophenyl)-3-(1-methylethyl)-1H-indol-2-yl]ethynyl]hydroxyphosphinyl]-3-hydroxybutanoic acid, methyl ester The title compound of Example 1; [[1-(4-fluorophenyl)-3-(1-methylethyl)-1H-indol-2-yl]-ethynyl]phosphinic acid (1.5 g) was suspended in xylenes (30 mL) under argon in a flame dried 3-necked flask. The suspension was cooled to 0° C. and triethylamine (680 μL) and trimethylchlorosilane (615 μL) were added. The solution was stirred for 5 minutes at 0° C. and then stirred for 90 minutes at room temperature. $^{31}$P-NMR revealed 100% monosilylation (−17.2 ppm).

The reaction mixture was cooled to 0° C. The title compound of Example 2 (S)-3-[(chlorodimethylsilyl)oxy]-4-iodo-butanoic acid, methyl ester (1.85 mL) was added slowly over 5 minutes. Triethylamine (740 μL) was then added slowly. The suspension turned yellow and was stirred for two hours at room temperature and then stirred for 18 hours at 125° C. The reaction was cooled to 0° C., quenched with 1N hydrochloric acid, and stirred at room temperature for one hour. The biphasic mixture was transferred to a separatory funnel. Ethyl acetate (200 mL) was added and the mixture was washed with 1N hydrochloic acid (3×30 mL), and brine (2×30 mL). The organic layer was dried (magnesium sulfate), filtered, and concentrated in vacuo to a light red solid.

EXAMPLE 4

(S)-4-[[[1-(4-Fluorophenyl)-3-(1-methylethyl)-1H-indol-2-yl]ethynyl]hydroxyphosphinyl]-3-hydroxybutanoic acid, methyl ester A. [[1-(4-Fluorophenyl)-3-(1-methylethyl)-1-H-indol-2-yl]ethynyl]phosphinic acid, ethyl ester To a solution of the title C compound of Example 1; 2-ethynyl-1-(4-fluorophenyl)-3-(1-methyethyl)-1H-indole (110 g, 0.397 mol) in dry tetrahydrofuran at −72° C. (acetone and dry ice bath) under an argon atmosphere was added with mechanical stirring, a 2.60M hexanes solution of n-butyl-lithium (150.6 mL, 0.391 mol) was added dropwise over a 50 minute period while maintaining the reaction temperature at approximately −75° C. (this was an exothermic addition). The resulting solution was stirred between −70° C. and −75° C. for an additional 15 minutes. Freshly distilled diethyl chlorophosphite (66 mL, 0.46 mol) was added dropwise (syringe) over 10 minutes to the above solution. The resultant solution was stirred between −71° C. and −75° C. for approximately 20 minutes and was then quenched with a saturated sodium bicarbonate solution (250 mL) and allowed to warm to room temperature. The starting material appeared gone by TLC (10% toluene/hexane). In a more polar solvent system (18:1:1 dichloromethane:acetic acid:methanol) the desired ethyl phosphinite was seen due to hydrolysis on the silica gel ($R_f$ approximately 0.8) as well as a small amount of the phosphinic acid ($R_f$ approximately 0.15).

The mixture was diluted with distilled water (330 mL) and ethyl acetate (670 mL). The aqueous phase was removed and extracted with ethyl acetate (350 mL×1). The organic phases were then combined, washed with a half-saturated sodium chloride solution (400 mL×2), brine (400 mL×1), dried over anhydrous sodium sulfate, and filtered. The filtrate was concentrated at reduced pressure to approximately half of its original volume (approximately 1 liter). Deionized water (8 mL) and para-toluenesulfonic acid (1.47 g, 0.008 mol) were added to the concentrated solution at room temperature, and the resultant solution was stirred for approximately 10 minutes. This hydrolysis was monitored by TLC (10% toluene/hexane) in which the intermediate phosphite could be observed ($R_f$ approximately 0.50) along with an unknown impurity ($R_f$ approximately 0.58; trace amount). The resultant solution was washed with a saturated sodium bicarbonate solution (100 mL×2), brine (100 mL×1), dried over anhydrous sodium sulfate, and concentrated to dryness at reduced pressure to obtain approximately 178 g of a dark, brown oil. This oil was dissolved in diethyl ether (115 mL) and diluted with hexane (300 mL). The ether was then removed in vacuo until a cloudy, white precipitate was seen forming. The mixture was kept at room temperature for approximately 10 minutes (some crystal formation was observed) and then in the cold room (4° C.) for approximately 12 hours. The resultant crop was filtered, and the crystals were washed with cold 2% ethyl acetate in hexane (200 mL) and dried under vacuum (approximately 1 mm Hg) to give the title compound as a beige solid in 76% yield (110.9 g), m.p. 80° C. to 82.5° C. 35 g of a second crop of crystals consisting of an approximately 1:1 mixture of the product and the phosphinic acid (proton NMR) along with another minor unknown impurity was obtained from the mother liquor.

B. (S)-4-[[[1-(4-Fluorophenyl)-3-(1-methylethyl)-1H-indol-2-yl]ethynyl]hydroxyphosphinyl]-3-hydroxybutanonic acid, methyl ester The title A compound (0.5 g) was dissolved in xylenes (10 mL) and cooled to 0° C. under argon. The title compound of Example 2; (S)-3-[(chlorodimethylsilyl)oxy]-4-iodo-butanoic acid, methyl ester (572 μL) was added followed by the slow addition of triethylamine (230 μL). The resulting mixture was stirred at room temperature for 40 minutes and then heated at 125° C. overnight. The reaction was cooled to 0° C. and quenched with 1N hydrochloric acid. The mixture was transferred to a separatory funnel and diluted with ethyl acetate. The layers were separated and the organic layer was washed with additional 1N hydrochloric acid and brine. The organic layer was dried (sodium sulfate), filtered and concentrated to a brown oil.

EXAMPLE 5

(S)-4-[[[1-(4-Fluorophenyl)-3-(1-methylethyl)-1H-indol-2-yl]ethynyl]hydroxyphosphinyl]-3-hydroxybutanoic acid, disodium salt A. (S)-4-[[[1-(4-Fluorophenyl)-3-(1-methylethyl)-1H-indol-2-yl]ethynyl]hydroxyphosphinyl]-3-hydroxybutanonic acid, methyl ester 1-adamantanamine salt The crude title compound of Example 3 (S)-4-[[[1-(4-fluorophenyl)-3-(1-methylethyl)-1H-indol-2-yl]ethynyl]hydroxyphosphinyl]-3-hydroxybutanoic acid, methyl ester (2 g) was dissolved in ethyl acetate (56 mL) and treated with a freshly filtered solution of 1-adamantanamine (823 mg, 5.28 mmol) in ethyl acetate (23 mL). The resulting slurry was stirred at room temperature under argon overnight. The product was filtered and washed with ethyl acetate and hexane and dried in vacuo to produce 2.02 g (77%) of the title compound.

B. (S)-4-[[[1-(4-Fluorophenyl)-3-(1-methylethyl)-1H-indol-2-yl]ethynyl]hydroxyphosphinyl]-3 -hydroxybutanoic acid, disodium salt To a suspension of the title A compound (4 g, 6.58 mmol) in double distilled water (9.6 mL) was added portionwise 1N sodium hydroxide (19.74 mL, 3 eq. 19.74 mmol) at room temperature with magnetic stirring. After five minutes, the suspension became clear and the stirring was continued for an additional 30 minutes. The solution was washed with hexane (10 mL×1), ether (20 mL×5), acidified with 1N hydrochloric acid to pH ~2, and then extracted with ethyl acetate (25 mL×2). The combined ethyl acetate layer was washed with half saturated sodium chloride (10 mL×1) and brine (10 mL×2), dried over sodium sulfate, filtered, concentrated, and dried under vacuum for ten minutes. The yellowish foam thus obtained was dissolved in premixed methanol:water; 2:1 (13 mL) solvent and titrated from pH 2.0 to 8.1 using 3N and 1N sodium hydroxide solution. The clear solution was concentrated to a foam and then azeotroped with acetonitrile (30 mL×2) to a solid residue. The solid (3.2 g) was then dissolved in water (4 mL) and methanol (8 mL). To this yellowish solution was added dropwise acetonitrile (56 mL) with vigorous stirring and the suspension was stirred overnight. The precipitate was filtered and washed with acetonitrile (20 mL×3) to give the title compound (3.0 g; 93.6%).

What is claimed is:

1. A process for the preparation of a compound of formula $$Z-X-\underset{\underset{OH}{|}}{\overset{\overset{O}{\|}}{P}}-CH_2\underset{\underset{}{|}}{\overset{\overset{OH}{|}}{C}}HCH_2COOR_1 \qquad I$$

or a pharmaceutically acceptable salt thereof; where X is $-CH_2-$, $-CH_2CH_2-$, $-CH_2CH_2CH_2-$, $-CH=CH-$, $-C\equiv C-$ or $-CH_2O-$ (where O is linked to Z); Z is a hydrophobic anchor; and $R_1$ is hydrogen, alkyl, cycloalkyl or aryl; comprising the steps of:

(A) preparing a compound of formula $$Y-CH_2-\overset{\overset{OR_2}{|}}{C}HCH_2COOR_1 \qquad II$$

where Y is iodine; $R_2$ is a radical of formula $-SiW(R_3)_2$ where W is chlorine, bromine, alkoxy or dialkylamine and $R_3$ is alkyl or cycloalkyl, by:

(1) treating a halohydrin of formula $$A-CH_2\overset{\overset{OH}{|}}{C}HCH_2COOR_1 \qquad III$$

where A is bromine or chlorine, with an iodide ion in an organic solvent to form an iodohydrin of formula $$I-CH_2-\overset{\overset{OH}{|}}{C}HCH_2COOR_1; \qquad IV$$

and (2) treating a compound of formula IV with a silane to form a compound of formula II;

(B) reacting a compound of formula II with a compound of formula $$Z-C\equiv C-\underset{\underset{OR_4}{|}}{\overset{\overset{O}{\|}}{P}}-H \qquad V$$

where $R_4$ is trialkylsilyl or triarylsilyl; or a compound of formula $$Z-C\equiv C-\underset{\underset{OR_3}{|}}{\overset{\overset{O}{\|}}{P}}-H \qquad VI$$

in the presence of an amine base or an alkali metal hydride in an organic solvent to form a compound having the formula $$Z-C\equiv C-\underset{\underset{O-Si(R_3)_2-O-\overset{|}{C}H}{|}}{P}-OR_5 \quad \underset{CH_2COOR_1}{\overset{CH_2Y}{|}} \qquad VII$$

where $R_5$ is $R_4$, when compounds of formula II are reacted with compounds of formula V; or $R_3$ when compounds of formula II are reacted with compounds of formula VI;

(C) heating the compound of formula VII at a temperature of from about 100° C. to about 200° C., to form a compound of formula $$Z-C\equiv C-\overset{\overset{O}{\|}}{\underset{\underset{Si}{\underset{|}{O}}}{P}}\diagdown \underset{(R_3)_2}{\overset{O}{\diagup}}CH_2COOR_1; \qquad VIII$$

and (D) quenching the compound of formula VIII with an acid to provide the compounds of formula I.

2. The method of claim 1 wherein a compound of formula II is reacted with a compound of formula V.

3. The method of claim 1 wherein a compound of formula II is reacted with a compound of formula VI.

4. A compound of the formula

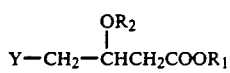

where Y is a halogen; $R_1$ is hydrogen, alkyl, cyclo-alkyl or aryl; and $R_2$ is a radical of formula $-SiW(R_3)_2$ where W is chlorine, bromine, alkoxy or dialkylamine and $R_3$ is alkyl or cycloalkyl.

5. A method of preparing a compound of formula

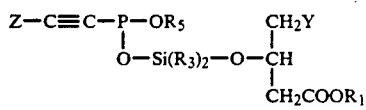

where Y is a halogen, preferably iodine; Z is hydrophobic anchor; $R_1$ is hydrogen, alkyl, cycloalkyl or aryl; $R_2$ is a radical of formula $-SiW(R_3)_2$ where W is chlorine, bromine, alkoxy or dialkylamine and $R_3$ is alkyl or cycloalkyl; and $R_5$ is $R_3$ or $R_4$ is trialkylsilyl or triarylsilyl; comprising the step of reacting a compound of formula

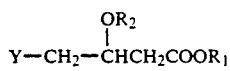

with a compound of formula

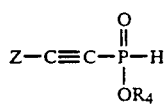

to form the compounds of formula VII where $R_5$ is $R_4$ or with compounds of formula

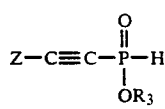

to form the compounds of formula VII where $R_5$ is $R_3$; in the presence of an amine base or an alkali metal hydride in an organic solvent.

6. A compound of the formula

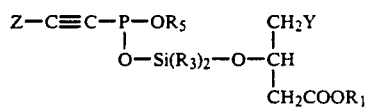

where Y is a halogen; Z is a hydrophobic anchor; $R_1$ is hydrogen, alkyl, cycloalkyl or aryl; $R_3$ is alkyl or cycloalkyl; and $R_5$ is $R_4$ or $R_3$, where $R_4$ is trialkylsilyl or triarylsilyl.

7. A method of preparing a compound of formula

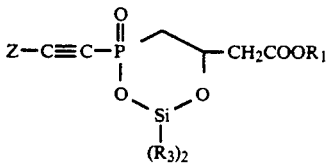

where Z is hydrophobic anchor; $R_1$ is hydrogen, alkyl, cycloalkyl or aryl; and $R_3$ is alkyl or cycloalkyl; comprising the step of heating a compound of formula

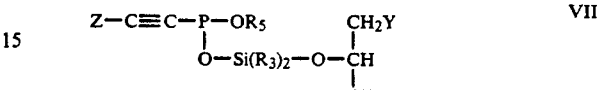

where Y is a halogen, and $R_5$ is $R_4$ or $R_3$, where $R_4$ is trialkylsilyl or triarylsilyl; at a temperature of from about 100° C. to about 200° C.

8. A compound of the formula

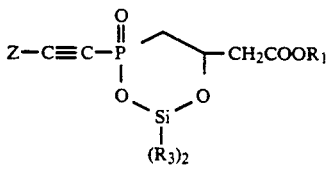

where Z is hydrophobic anchor; $R_1$ is hydrogen, alkyl, cycloalkyl or aryl; and $R_3$ is alkyl or cycloalkyl.

9. A process for the preparation of a compound of formula

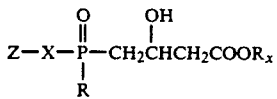

or a salt thereof, where X is $-CH_2-$, $-CH_2CH_2-$, $-CH_2CH_2CH_2-$, $-CH=CH-$, $-C\equiv C-$ or $-CH_2O-$ (where O is linked to Z); Z is a hydrophobic anchor; R is hydroxy or lower alkoxy; and $R_x$ is hydrogen or lower alkyl, comprising the steps of:

(A) preparing a compound of the formula

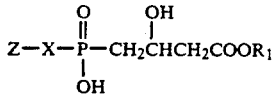

or a salt thereof wherein $R_1$ is hydrogen or lower alkyl; and (B) converting said compound of the formula I or a salt thereof to said compound of the formula A or a salt thereof, with the proviso that said compound of formula I or a salt thereof is prepared by the process of claim 1.

10. A process for the preparation of a compound of formula

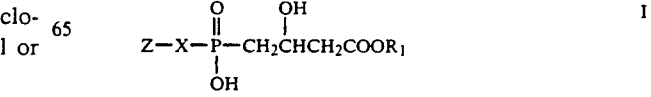

or a pharmaceutically acceptable salt thereof; where X is $-CH_2-$, $-CH_2CH_2-$, $-CH_2CH_2CH_2-$, $-CH=CH-$, $-C\equiv C-$ or $-CH_2O-$ (where O is linked to Z); Z is a hydrophobic anchor; and $R_1$ is hydrogen, alkyl, cycloalkyl or aryl; comprising the steps of:

(A) preparing a compound of formula

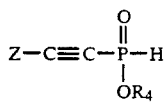
II where Y is a halogene; $R_2$ is a radical of formula $-SiW(R_3)_2$ where W is chlorine, bromine, alkoxy or dialkylamine and $R_3$ is alkyl or cycloalkyl;

(B) reacting a compound of formula II with a compound of formula

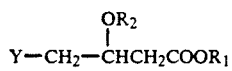
V where $R_4$ is trialkylsilyl or triarylsilyl; or a compound of formula

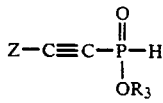
VI in the presence of an amine base or an alkali metal hydride in an organic solvent to form a compound having the formula

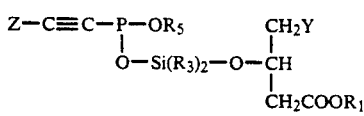
VII where $R_5$ is $R_4$, when compounds of formula II are reacted with compounds of formula V; or $R_3$ when compounds of formula II are reacted with compounds of formula VI;

(C) heating the compound of formula VII at a temperature of from about 100° C. to about 200° C., to form a compound of formula

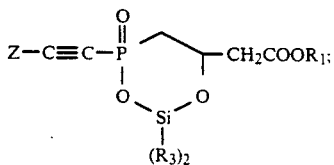
VIII and (D) quenching the compound of formula VIII with an acid to provide the compounds of formula I.

* * * * *

UNITED STATES PATENT AND TRADEMARK OFFICE
CERTIFICATE OF CORRECTION

PATENT NO.   :   5,274,155
DATED        :   December 28, 1993
INVENTOR(S)  :   J.K. Thottathil et al.

It is certified that error appears in the above-identified patent and that said Letters Patent is hereby corrected as shown below:

In Claim 5, column 19, line 27, after the word "$R_4$", insert the words -- where $R_4$ --.

Signed and Sealed this

Twenty-eighth Day of June, 1994

Attest:

BRUCE LEHMAN

*Attesting Officer*    *Commissioner of Patents and Trademarks*